(12) United States Patent
Dreher

(10) Patent No.: US 9,050,203 B2
(45) Date of Patent: *Jun. 9, 2015

(54) BENDABLE STENT

(71) Applicant: C. R. Bard, Inc., Murray Hill, NJ (US)

(72) Inventor: Gael Dreher, Karlsruhe (DE)

(73) Assignee: C. R. BARD, INC., Murray Hills, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/975,147

(22) Filed: Aug. 23, 2013

(65) Prior Publication Data

US 2013/0345791 A1    Dec. 26, 2013

Related U.S. Application Data

(63) Continuation of application No. 12/594,531, filed as application No. PCT/EP2008/054007 on Apr. 3, 2008, now Pat. No. 8,518,101.

(30) Foreign Application Priority Data

Apr. 3, 2008    (GB) .................................. 0706499.1

(51) Int. Cl.
  *A61F 2/06*    (2013.01)
  *A61F 2/915*    (2013.01)
  (Continued)

(52) U.S. Cl.
  CPC . *A61F 2/915* (2013.01); *A61F 2/89* (2013.01); *A61F 2/91* (2013.01);
  (Continued)

(58) Field of Classification Search
  CPC ............... A61F 2/88; A61F 2/89; A61F 2/91; A61F 2/915; A61F 2230/0054
  USPC ....................................... 623/1.15, 1.22, 1.34
  See application file for complete search history.

(56) References Cited

U.S. PATENT DOCUMENTS 5,091,205 A    2/1992    Fan
5,464,419 A    11/1995    Glastra
(Continued)

FOREIGN PATENT DOCUMENTS

DE    04130431 A1    3/1993
DE    29621207 U1    1/1997
(Continued)

OTHER PUBLICATIONS

U.S. Appl. No. 10/362,040, filed Jun. 27, 2003 Office Action dated Aug. 2, 2006.
(Continued)

*Primary Examiner* — Kathleen Holwerda
*Assistant Examiner* — Sarah W Aleman
(74) *Attorney, Agent, or Firm* — Buchalter Nemer

(57) ABSTRACT

A stent includes a matrix of struts. The matrix of struts may be disposed parallel to one another in a non-expanded disposition. A plurality of loops along the longitudinal axis may be formed by the matrix of struts. In one aspect, a plurality of cusps in each loop of the plurality of loops connects adjacent struts, the plurality of cusps including tied cusps and free cusps. The tied cusps of one loop can be connected to the tied cusps of an adjacent loop by a bridge extending therebetween. In one aspect, the adjacent struts connected by a tied cusp have different lengths. In one aspect, at least one free cusp in each loop joins two struts of approximately equal length.

12 Claims, 5 Drawing Sheets

(51) Int. Cl.
*A61F 2/89* (2013.01)
*A61F 2/91* (2013.01)

(52) U.S. Cl.
CPC ............. *A61F 2002/91508* (2013.01); *A61F 2002/91533* (2013.01); *A61F 2002/91558* (2013.01); *A61F 2230/0054* (2013.01)

(56) References Cited

U.S. PATENT DOCUMENTS

| | | | |
|---|---|---|---|
| 5,527,353 A | 6/1996 | Schmitt | |
| 5,591,223 A | 1/1997 | Lock et al. | |
| 5,645,532 A | 7/1997 | Horgan | |
| 5,725,572 A | 3/1998 | Lam et al. | |
| 5,741,327 A | 4/1998 | Frantzen | |
| 5,759,192 A | 6/1998 | Saunders | |
| 5,800,511 A | 9/1998 | Mayer | |
| 5,824,042 A | 10/1998 | Lombardi et al. | |
| 5,824,059 A | 10/1998 | Wijay | |
| 5,824,077 A | 10/1998 | Mayer | |
| 5,843,118 A | 12/1998 | Sepetka et al. | |
| 5,858,556 A | 1/1999 | Eckert et al. | |
| 5,861,027 A | 1/1999 | Trapp | |
| 5,868,783 A | 2/1999 | Tower | |
| 5,922,020 A | 7/1999 | Klein et al. | |
| 6,022,374 A | 2/2000 | Imran | |
| 6,053,940 A | 4/2000 | Wijay | |
| 6,056,187 A | 5/2000 | Acciai et al. | |
| 6,086,611 A | 7/2000 | Duffy et al. | |
| 6,099,561 A | 8/2000 | Alt | |
| 6,174,329 B1 | 1/2001 | Callol et al. | |
| 6,241,762 B1 | 6/2001 | Shanley | |
| 6,270,524 B1 | 8/2001 | Kim | |
| 6,293,966 B1 | 9/2001 | Frantzen | |
| 6,312,456 B1 | 11/2001 | Kranz et al. | |
| 6,334,871 B1 | 1/2002 | Dor et al. | |
| 6,355,057 B1 | 3/2002 | DeMarais et al. | |
| 6,379,381 B1 | 4/2002 | Hossainy et al. | |
| 6,387,123 B1 | 5/2002 | Jacobs et al. | |
| 6,409,752 B1 | 6/2002 | Boatman et al. | |
| 6,451,047 B2 | 9/2002 | McCrea et al. | |
| 6,471,721 B1 | 10/2002 | Dang | |
| 6,475,233 B2 | 11/2002 | Trozera | |
| 6,478,816 B1 | 11/2002 | Kveen et al. | |
| 6,540,777 B2 | 4/2003 | Stenzel et al. | |
| 6,547,818 B1 | 4/2003 | Rourke et al. | |
| 6,562,065 B1 | 5/2003 | Shanley | |
| 6,585,757 B1 | 7/2003 | Callol | |
| 6,605,110 B2 | 8/2003 | Harrison | |
| 6,629,994 B2 | 10/2003 | Gomez et al. | |
| 6,676,700 B1 | 1/2004 | Jacobs et al. | |
| 6,770,089 B1 | 8/2004 | Hong et al. | |
| 6,797,217 B2 | 9/2004 | McCrea et al. | |
| 6,827,734 B2 | 12/2004 | Fariabi | |
| 6,878,162 B2 | 4/2005 | Bales et al. | |
| 6,979,346 B1 | 12/2005 | Hossainy et al. | |
| 7,060,093 B2 | 6/2006 | Dang et al. | |
| 7,135,038 B1 | 11/2006 | Limon | |
| 7,175,654 B2 | 2/2007 | Bonsignore et al. | |
| 7,381,217 B2 * | 6/2008 | Tischler | 623/1.16 |
| 7,462,190 B2 | 12/2008 | Lombardi | |
| 7,468,071 B2 | 12/2008 | Edwin et al. | |
| 7,479,157 B2 | 1/2009 | Weber et al. | |
| 7,691,461 B1 | 4/2010 | Prabhu | |
| 7,771,463 B2 | 8/2010 | Ton et al. | |
| 7,772,659 B2 | 8/2010 | Rodmacq et al. | |
| 8,043,364 B2 | 10/2011 | Lombardi et al. | |
| 8,152,842 B2 | 4/2012 | Schlun | |
| 8,292,950 B2 | 10/2012 | Dorn et al. | |
| 8,322,593 B2 | 12/2012 | Wack | |
| 8,403,978 B2 | 3/2013 | Schlun et al. | |
| 8,475,520 B2 | 7/2013 | Wack et al. | |
| 8,518,101 B2 | 8/2013 | Dreher | |
| 2002/0007212 A1* | 1/2002 | Brown et al. | 623/1.16 |
| 2002/0116044 A1 | 8/2002 | Cottone et al. | |
| 2002/0116051 A1 | 8/2002 | Cragg | |
| 2002/0138136 A1 | 9/2002 | Chandresekaran et al. | |
| 2002/0193867 A1 | 12/2002 | Gladdish et al. | |
| 2002/0193869 A1 | 12/2002 | Dang | |
| 2002/0198589 A1 | 12/2002 | Leong | |
| 2003/0055485 A1 | 3/2003 | Lee et al. | |
| 2003/0135254 A1 | 7/2003 | Curcio et al. | |
| 2003/0144725 A1 | 7/2003 | Lombardi | |
| 2003/0216807 A1 | 11/2003 | Jones et al. | |
| 2003/0225448 A1 | 12/2003 | Gerberding | |
| 2004/0015228 A1 | 1/2004 | Lombardi et al. | |
| 2004/0015229 A1 | 1/2004 | Fulkerson et al. | |
| 2004/0034402 A1 | 2/2004 | Bales et al. | |
| 2004/0044401 A1 | 3/2004 | Bales et al. | |
| 2004/0073290 A1* | 4/2004 | Chouinard | 623/1.15 |
| 2004/0073291 A1* | 4/2004 | Brown et al. | 623/1.15 |
| 2004/0117002 A1 | 6/2004 | Girton et al. | |
| 2004/0230293 A1 | 11/2004 | Yip et al. | |
| 2004/0236400 A1 | 11/2004 | Edwin et al. | |
| 2004/0236409 A1 | 11/2004 | Pelton et al. | |
| 2004/0254637 A1 | 12/2004 | Yang et al. | |
| 2005/0049682 A1 | 3/2005 | Leanna et al. | |
| 2005/0060025 A1 | 3/2005 | Mackiewicz et al. | |
| 2005/0149168 A1 | 7/2005 | Gregorich | |
| 2005/0172471 A1 | 8/2005 | Vietmeier | |
| 2005/0182477 A1 | 8/2005 | White | |
| 2005/0222667 A1 | 10/2005 | Hunt | |
| 2005/0278019 A1 | 12/2005 | Gregorich | |
| 2006/0030934 A1 | 2/2006 | Hogendijk et al. | |
| 2006/0064153 A1 | 3/2006 | Langhans et al. | |
| 2006/0216431 A1 | 9/2006 | Kerrigan | |
| 2006/0241741 A1 | 10/2006 | Lootz | |
| 2006/0265049 A1 | 11/2006 | Gray et al. | |
| 2007/0112421 A1 | 5/2007 | O'Brien | |
| 2007/0219624 A1 | 9/2007 | Brown et al. | |
| 2008/0051885 A1 | 2/2008 | Llanos et al. | |
| 2008/0188924 A1 | 8/2008 | Prabhu | |
| 2009/0125092 A1 | 5/2009 | McCrea et al. | |
| 2009/0125099 A1 | 5/2009 | Weber et al. | |
| 2009/0200360 A1 | 8/2009 | Wack | |
| 2009/0204201 A1 | 8/2009 | Wack | |
| 2009/0204203 A1 | 8/2009 | Allen et al. | |
| 2009/0264982 A1 | 10/2009 | Krause et al. | |
| 2010/0016949 A1 | 1/2010 | Wack | |
| 2010/0070021 A1 | 3/2010 | Wack et al. | |
| 2010/0114298 A1 | 5/2010 | Dorn et al. | |
| 2010/0191321 A1 | 7/2010 | Schlun et al. | |
| 2010/0204784 A1 | 8/2010 | Molaei et al. | |
| 2010/0211161 A1 | 8/2010 | Dreher | |
| 2010/0234936 A1 | 9/2010 | Schlun | |
| 2010/0249903 A1 | 9/2010 | Wack et al. | |
| 2010/0298921 A1 | 11/2010 | Schlun et al. | |
| 2011/0196473 A1 | 8/2011 | McCrea et al. | |
| 2011/0198327 A1 | 8/2011 | Prabhu | |
| 2011/0245905 A1 | 10/2011 | Weber et al. | |
| 2011/0319977 A1 | 12/2011 | Pandelidis et al. | |
| 2012/0041542 A1 | 2/2012 | Lombardi et al. | |

FOREIGN PATENT DOCUMENTS

| | | |
|---|---|---|
| DE | 19728337 A1 | 1/1999 |
| DE | 29904817 U1 | 5/1999 |
| DE | 10201151 A1 | 7/2003 |
| DE | 202004014789 U1 | 1/2005 |
| DE | 102004045994 A1 | 3/2006 |
| EP | 0481365 A1 | 4/1992 |
| EP | 0709068 A2 | 5/1996 |
| EP | 0800800 A1 | 10/1997 |
| EP | 0847733 A1 | 6/1998 |
| EP | 0870483 A2 | 10/1998 |
| EP | 1029517 A2 | 8/2000 |
| EP | 1034751 A2 | 9/2000 |
| EP | 1157673 A2 | 11/2001 |
| EP | 1190685 A2 | 3/2002 |
| EP | 1212991 A2 | 6/2002 |
| EP | 1245203 A2 | 10/2002 |
| EP | 1255507 A1 | 11/2002 |
| EP | 1356789 A1 | 10/2003 |
| EP | 1433438 A2 | 6/2004 |

(56) References Cited

FOREIGN PATENT DOCUMENTS

| | | |
|---|---|---|
| EP | 1488763 A2 | 12/2004 |
| EP | 1767240 A1 | 3/2007 |
| EP | 2134301 A2 | 12/2009 |
| FR | 2626046 A1 | 7/1989 |
| GB | 453944 A | 9/1936 |
| JP | 07315147 A | 12/1995 |
| JP | 2004-506477 A | 3/2004 |
| JP | 2007-504891 A | 3/2007 |
| JP | 4827965 B2 | 11/2011 |
| JP | 4933018 B2 | 5/2012 |
| WO | 9417754 A1 | 8/1994 |
| WO | 9503010 A1 | 2/1995 |
| WO | 9626689 A1 | 9/1996 |
| WO | 9733534 A1 | 9/1997 |
| WO | 9820810 A1 | 5/1998 |
| WO | 9915108 A2 | 4/1999 |
| WO | 9938457 A1 | 8/1999 |
| WO | 9949928 A1 | 10/1999 |
| WO | 9955253 A1 | 11/1999 |
| WO | 0045742 A1 | 8/2000 |
| WO | 0049971 A1 | 8/2000 |
| WO | 0064375 A1 | 11/2000 |
| WO | 0101889 A1 | 1/2001 |
| WO | 0132102 A1 | 5/2001 |
| WO | 0158384 A1 | 8/2001 |
| WO | 0176508 A2 | 10/2001 |
| WO | 0215820 A2 | 2/2002 |
| WO | 0249544 A1 | 6/2002 |
| WO | 03055414 A1 | 7/2003 |
| WO | 03075797 | 9/2003 |
| WO | 03101343 A1 | 12/2003 |
| WO | 2004019820 A1 | 3/2004 |
| WO | 2004028408 A1 | 4/2004 |
| WO | 2004032802 A2 | 4/2004 |
| WO | 2004058384 A1 | 7/2004 |
| WO | 2005067816 A1 | 7/2005 |
| WO | 2005072652 A1 | 8/2005 |
| WO | 2005104991 A1 | 11/2005 |
| WO | 2005032403 A3 | 12/2005 |
| WO | 2006010636 A1 | 2/2006 |
| WO | 2006010638 A1 | 2/2006 |
| WO | 2006014768 A1 | 2/2006 |
| WO | 2006025847 A2 | 3/2006 |
| WO | 2006036912 A2 | 4/2006 |
| WO | 2006047977 A1 | 5/2006 |
| WO | 2006064153 A1 | 6/2006 |
| WO | 2007073413 A1 | 6/2007 |
| WO | 2006026778 A3 | 11/2007 |
| WO | 2007131798 A1 | 11/2007 |
| WO | 2007135090 A1 | 11/2007 |
| WO | 2008006830 A1 | 1/2008 |
| WO | 2008022949 A1 | 2/2008 |
| WO | 2008022950 A1 | 2/2008 |
| WO | 2008025762 A1 | 3/2008 |
| WO | 2008028964 A2 | 3/2008 |
| WO | 2008055980 A1 | 5/2008 |
| WO | 2008068279 A1 | 6/2008 |
| WO | 2008101987 A1 | 8/2008 |
| WO | 2008119837 A2 | 10/2008 |
| WO | 2009030748 A2 | 3/2009 |

OTHER PUBLICATIONS

U.S. Appl. No. 10/362,040, filed Jun. 27, 2003 Office Action dated Dec. 10, 2007.
U.S. Appl. No. 10/362,040, filed Jun. 27, 2003 Office Action dated Feb. 23, 2010.
U.S. Appl. No. 10/362,040, filed Jun. 27, 2003 Office Action dated Jan. 10, 2006.
U.S. Appl. No. 10/362,040, filed Jun. 27, 2003 Office Action dated Jul. 15, 2009.
U.S. Appl. No. 10/362,040, filed Jun. 27, 2003 Office Action dated Jun. 23, 2005.
U.S. Appl. No. 10/362,040, filed Jun. 27, 2003 Office Action dated Jun. 5, 2007.
U.S. Appl. No. 12/300,985, filed Aug. 6, 2010 Final Office Action dated Aug. 15, 2012.
U.S. Appl. No. 12/300,985, filed Aug. 6, 2010 Non-Final Office Action dated Mar. 15, 2012.
U.S. Appl. No. 12/300,985, filed Aug. 6, 2010 Notice of Allowance dated Nov. 16, 2012.
U.S. Appl. No. 12/301,019, filed Feb. 2, 2009 Advisory Action dated Apr. 27, 2011.
U.S. Appl. No. 12/301,019, filed Feb. 2, 2009 Final Office Action dated Feb. 7, 2011.
U.S. Appl. No. 12/301,019, filed Feb. 2, 2009 Non-Final Office Action dated Sep. 3, 2010.
U.S. Appl. No. 12/373,116, filed Jul. 14, 2009 Advisory Action dated Jul. 26, 2011.
U.S. Appl. No. 12/373,116, filed Jul. 14, 2009 Examiner's Answer dated Jan. 3, 2013.
U.S. Appl. No. 12/373,116, filed Jul. 14, 2009 Final Office Action dated Apr. 27, 2011.
U.S. Appl. No. 12/373,116, filed Jul. 14, 2009 Final Office Action dated Mar. 29, 2012.
U.S. Appl. No. 12/373,116, filed Jul. 14, 2009 Non-Final Office Action dated Nov. 10, 2010.
U.S. Appl. No. 12/373,116, filed Jul. 14, 2009 Non-Final Office Action dated Nov. 18, 2011.
U.S. Appl. No. 12/373,116, filed Jul. 14, 2009 Notice of Panel Decision dated Aug. 20, 2012.
U.S. Appl. No. 12/438,102, filed Feb. 19, 2009 Non-Final Office Action dated Nov. 15, 2010.
U.S. Appl. No. 12/438,330, filed Feb. 20, 2009 Advisory Action dated Oct. 14, 2010.
U.S. Appl. No. 12/438,330, filed Feb. 20, 2009 Advisory Action dated Oct. 20, 2011.
U.S. Appl. No. 12/438,330, filed Feb. 20, 2009 Final Office Action dated Aug. 11, 2011.
U.S. Appl. No. 12/438,330, filed Feb. 20, 2009 Non-Final Office Action dated Jun. 7, 2012.
U.S. Appl. No. 12/438,330, filed Feb. 20, 2009 Notice of Allowance dated Sep. 25, 2012.
U.S. Appl. No. 12/438,330, filed Feb. 20, 2009 Office Action dated Aug. 5, 2010.
U.S. Appl. No. 12/438,330, filed Feb. 20, 2009 Office Action dated Mar. 16, 2010.
U.S. Appl. No. 12/438,330, filed Feb. 20, 2009 Office Action dated Mar. 4, 2011.
U.S. Appl. No. 12/438,527, filed Feb. 23, 2009 Advisory Action dated May 24, 2012.
U.S. Appl. No. 12/438,527, filed Feb. 23, 2009 Final Office Action dated Mar. 7, 2012.
U.S. Appl. No. 12/438,527, filed Feb. 23, 2009 Non-Final Office Action dated Jul. 11, 2011.
U.S. Appl. No. 12/440,415, filed Mar. 6, 2009 Final Office Action dated Jan. 10, 2013.
U.S. Appl. No. 12/440,415, filed Mar. 6, 2009 Non-Final Office Action dated Jul. 2, 2012.
U.S. Appl. No. 12/440,415, filed Mar. 6, 2009 Notice of Allowance dated Apr. 3, 2013.
U.S. Appl. No. 12/514,177, filed May 8, 2009 Advisory Action dated Sep. 10, 2012.
U.S. Appl. No. 12/514,177, filed May 8, 2009 Final Office Action dated Apr. 27, 2011.
U.S. Appl. No. 12/514,177, filed May 8, 2009 Final Office Action dated Jul. 11, 2012.
U.S. Appl. No. 12/514,177, filed May 8, 2009 Non-Final Office Action dated Jan. 5, 2011.
U.S. Appl. No. 12/514,177, filed May 8, 2009 Non-Final Office Action dated Mar. 13, 2012.
U.S. Appl. No. 12/517,096, filed Jun. 1, 2009 Final Office Action dated Oct. 31, 2011.
U.S. Appl. No. 12/517,096, filed Jun. 1, 2009 Non-Final Office Action dated Jun. 18, 2012.
U.S. Appl. No. 12/517,096, filed Jun. 1, 2009 Non-Final Office Action dated May 6, 2011.

(56) References Cited

OTHER PUBLICATIONS

U.S. Appl. No. 12/517,096, filed Jun. 1, 2009 Non-Final Office Action dated Nov. 28, 2012.
U.S. Appl. No. 12/517,096, filed Jun. 1, 2009 Notice of Panel Decision dated Mar. 23, 2012.
U.S. Appl. No. 12/528,289, filed Aug. 26, 2009 Non-Final Office Action dated Jan. 27, 2012.
U.S. Appl. No. 12/594,531, filed Oct. 2, 2009 Advisory Action dated Jan. 10, 2012.
U.S. Appl. No. 12/594,531, filed Oct. 2, 2009 Final Office Action dated Nov. 4, 2011.
U.S. Appl. No. 12/594,531, filed Oct. 2, 2009 Non-Final Office Action dated Dec. 17, 2010.
U.S. Appl. No. 12/594,531, filed Oct. 2, 2009 Non-Final Office Action dated May 12, 2011.
U.S. Appl. No. 12/594,531, filed Oct. 2, 2009 Non-Final Office Action dated Oct. 2, 2012.
U.S. Appl. No. 12/676,584, filed Mar. 4, 2010 Non-Final Office Action dated May 24, 2013.
U.S. Appl. No. 13/279,189, filed Oct. 21, 2011 Final Office Action dated May 2, 2013.
U.S. Appl. No. 13/279,189, filed Oct. 21, 2011 Non-Final Office Action dated Oct. 17, 2012.
Database Wikipedia, Sep. 11, 2007, "Lumen (anatomy)" XP 002453737 abstract.
EP 07787316.4 filed Jul. 10, 2007 Examination Report dated Dec. 23, 2011.
EP 07802603.6 filed Aug. 14, 2007 Office Action dated Dec. 13, 2010.
EP 07820066.4 filed Mar. 31, 2009 Examination Report dated Dec. 27, 2011.
EP 09177588 filed Aug. 14, 2007 Search Report dated Aug. 12, 2011.
EP 12174308.2 filed Apr. 3, 2008 European Search Report dated Sep. 10, 2012.
JP 2010-523512 filed Sep. 5, 2008 Office Action dated Sep. 25, 2012.
PCT/EP2001/009467 International Preliminary Examination Report Sep. 17, 2002.
PCT/EP2001/009467 International Search Report dated Feb. 18, 2002.
PCT/EP2007/004407 filed May 16, 2007 International Preliminary Report on Patentability dated Sep. 29, 2008.
PCT/EP2007/004407 filed May 16, 2007 Search Report dated Sep. 26, 2007.
PCT/EP2007/004407 filed May 16, 2007 Written Opinion dated Sep. 26, 2007.
PCT/EP2007/054822 filed on May 18, 2007 International Preliminary Report on Patentability dated Nov. 18, 2008.
PCT/EP2007/054822 filed on May 18, 2007 Search Report dated Sep. 18, 2007.
PCT/EP2007/054822 filed on May 18, 2007 Written Opinion dated Nov. 18, 2008.
PCT/EP2007/057041 filed Jul. 10, 2007 International Preliminary Report on Patentability dated Jan. 13, 2009.
PCT/EP2007/057041 filed Jul. 10, 2007 International Search Report dated Oct. 18, 2007.
PCT/EP2007/057041 filed Jul. 10, 2007 Written Opinion Jan. 10, 2009.
PCT/EP2007/058415 filed on Aug. 14, 2007 International Preliminary Report on Patentability dated Feb. 24, 2009.
PCT/EP2007/058415 filed on Aug. 14, 2007 Search Report dated Nov. 30, 2007.
PCT/EP2007/058415 filed on Aug. 14, 2007 Written Opinion dated Nov. 30, 2007.
PCT/EP2007/058416 filed Aug. 14, 2007 International Preliminary Report on Patentability dated Feb. 24, 2009.
PCT/EP2007/058416 filed Aug. 14, 2007 International Search Report dated Nov. 22, 2007.
PCT/EP2007/058416 filed Aug. 14, 2007 Written Opinion dated Feb. 23, 2009.
PCT/EP2007/058912 filed on Aug. 28, 2007 International Preliminary Report on Patentability dated Nov. 5, 2008.
PCT/EP2007/058912 filed on Aug. 28, 2007 Search Report dated Nov. 12, 2007.
PCT/EP2007/058912 filed on Aug. 28, 2007 Written Opinion dated Nov. 12, 2007.
PCT/EP2007/059407 filed Sep. 7, 2007 International Preliminary Report on Patentability and Written Opinion dated Mar. 10, 2009.
PCT/EP2007/059407 filed Sep. 7, 2007 International Search Report dated Jul. 3, 2008.
PCT/EP2007/059407 filed Sep. 7, 2007 Written Opinion dated Mar. 10, 2009.
PCT/EP2007/062155 filed on Nov. 9, 2007 Search Report dated Mar. 12, 2008.
PCT/EP2007/062155 filed on Nov. 9, 2007 Written Opinion dated Mar. 12, 2009.
PCT/EP2007/062155 filed on Novermber 9, 2007 International Preliminary Report on Patentability dated Oct. 15, 2008.
PCT/EP2007/063347 filed Dec. 5, 2007 Search Report dated Jun. 10, 2009.
PCT/EP2007/063347 filed Dec. 5, 2007 Written Opinion mailed Jun. 10, 2009.
PCT/EP2007/063347 filed on Dec. 5, 2007 Search Report mailed Feb. 4, 2008.
PCT/EP2008/052121 filed Feb. 21, 2008 International Preliminary Report on Patentability dated Aug. 26, 2009.
PCT/EP2008/052121 filed Feb. 21, 2008 International Search Report dated May 19, 2008.
PCT/EP2008/052121 filed Feb. 21, 2008 Written Opinion dated May 9, 2008.
PCT/EP2008/054007 filed Apr. 3, 2008 International Preliminary Report on Patentability dated Jul. 27, 2009.
PCT/EP2008/054007 filed Apr. 3, 2008 Search Report dated Jan. 30, 2009.
PCT/EP2008/054007 filed Apr. 3, 2008 Written Opinion dated Jan. 30, 2009.
PCT/EP2008/061775 filed Sep. 5, 2008 International Search Report dated Apr. 22, 2009.
PCT/EP2008/061775 filed Sep. 5, 2008 Written Opinion dated Apr. 22, 2009.
U.S. Appl. No. 10/362,040, filed Jun. 27, 2003 Advisory Action dated Dec. 16, 2010.
U.S. Appl. No. 10/362,040, filed Jun. 27, 2003 Advisory Action dated Jan. 9, 2009.
U.S. Appl. No. 10/362,040, filed Jun. 27, 2003 Advisory Action dated Nov. 29, 2006.
U.S. Appl. No. 10/362,040, filed Jun. 27, 2003 Final Office Action dated Aug. 30, 2010.
U.S. Appl. No. 10/362,040, filed Jun. 27, 2003 Notice of Allowance dated Jun. 22, 2011.
U.S. Appl. No. 10/362,040, filed Jun. 27, 2003 Office Action dated Aug. 18, 2008.

\* cited by examiner

BENDABLE STENT

PRIORITY

This application is a continuation of U.S. patent application Ser. No. 12/594,531, filed Dec. 7, 2009, now U.S. Pat. No. 8,518,101, which is a U.S. national stage application under 35 USC §371 of International Application No. PCT/EP2008/054007, filed Apr. 3, 2008, claiming priority to United Kingdom Patent Application No. 0706499.1, filed Apr. 3, 2007, each of which is incorporated by reference in its entirety into this application.

FIELD OF THE INVENTION

This invention relates to radially expansible stents for transluminal delivery to a stenting site within the body of a patient, the stent having an enhanced capacity for bending, after deployment in the body.

There are some stenting sites within the body in which there is substantial deformation of the lumen that is stented. Consider, for example, a peripheral vascular stent at a site near the knee. When an expanded stent suffers severe bending, there can be buckling on the inside of the bend. Even before there is any catastrophic buckling, the likelihood exists that portions of the stent matrix, spaced apart along the axis of the stent lumen, will approach each other and impact, on the inside of any temporary tight bend, to the detriment not only of the tissue caught between the impacting portions of the stent, but also the stent matrix itself. It is an object to the present invention to ameliorate this problem.

BACKGROUND OF THE INVENTION

The present applicant is a specialist in the manufacture of stents of nickel-titanium shape memory alloy, manufactured from a raw material that is a tubular workpiece of that alloy. To make the stent matrix, the alloy tube workpiece is subjected to a laser-cutting step in which the laser cuts a multiplicity of slits in the tubular workpiece. Each slit extends through the entire wall thickness of the tube, and for the most part, the slits all have the same length and are all parallel to the longitudinal axis of the tubular workpiece. When one advances around the circumference of the tubular workpiece, crossing transversely over a multiplicity of the slits, one by one, alternate slits that one crosses are staggered, in the axial direction of the tube, by a distance that is around half the length of each slit. When such a slitted tube is slipped over a mandrel, and expanded radially, each slit opens out into a diamond-shaped aperture in the wall thickness of the tube. Looked at in another way, the creation of the slits at the same time creates struts of material that lie between adjacent slits, and the struts in the radially expanded tube emerge as zig-zag stenting rings with a characteristic strut length within any one zig-zag ring that is more or less half the length of each of the slits cut by the laser.

Where two struts, next adjacent within the circumference of a zig-zag ring, come together, we can call this a "cusp". The cusps of each zig-zag ring are contiguous with cusps of the next adjacent stenting ring.

For enhanced flexibility of the zig-zag stent matrix, many of the "connector portions" between facing cusps of adjacent zig-zag stenting rings can be parted, to leave only a few (typically four or less) connector bridges between any two axially adjacent zig-zag stenting rings. See our WO 94/17754. The surviving connector bridges have a length direction parallel to the longitudinal axis of the stent matrix.

However where these connector bridges have been removed, there are still cusps of adjacent zig-zag stenting rings that are effectively "head to head" across the narrow gap with a cusp belonging to the adjacent zig-zag ring. When such a narrow gap is on the inside of the bend, upon bending the expanded stent (by movement of the body after the stent has been placed in the body), there is the likelihood of the two cusps head to head impacting on each other. It is common to call this "peak to peak".

In this discussion, it is important to distinguish between the radially compact trans-luminal delivery disposition of the stent matrix (not very different from the as-cut disposition of the stent matrix, before expansion on the mandrel to diamond-shaped apertures) and the radially expanded and deployed configuration of the stent, where the struts form zig-zag rings. A head to head facing configuration of parted connector portion cusps is tolerable for the delivery procedure but to be avoided, if that is feasible, after stent deployment and radial expansion.

The present applicant has been interested in this objective for some years. For a previous proposal for improvements see its WO 01/76508/ published Oct. 18, 2001. The present invention represents a fresh approach to the problem and, it is thought, a more elegant solution.

Other makers of stents have concerned themselves with the same objective. See for example US 2004/0073290 A1 where {paragraph 0002) it is explained that "if adjacent rings are spaced too close together" then "interference can occur between adjacent rings on the inside of a bend". Clearly, the idea of spacing the axially adjacent rings further apart has limited appeal/because it leaves the space between the rings unstented.

Self-expanding stents of nickel-titanium shape memory alloy are not particularly radiopaque and so are often equipped with radiopaque markers, of which one favoured material is tantalum because it is close to the nickel-titanium alloy in electrochemical potential/thereby minimising galvanic corrosion in the electrolyte of a bodily fluid.

Self-expanding stents are usually deployed by proximal withdrawal of a sheath of a catheter delivery system. To prevent the stent moving proximally with the withdrawing sheath it is conventional to use a pushing annulus, that abuts the proximal end zone of the stent and resists any proximal movement of the stent relative to the stent delivery catheter as such. As stent performance and length go up so does the compressive stress imposed on the end zone of the stent by the pushing annulus during withdrawal. It is important to avoid imposing on any part of the end zone a magnitude of stress higher than that of the design performance limits for that stent. The present inventor knows that one way to manage that peak stress is to build the stent so that the end zone has all its cusps touching a notional circle transverse to the longitudinal axis of the stent, so that the stress from the pushing annulus is shared equally amongst all those cusps. For an example of a stent with such an end zone, see WO 2006/047977.

EP-A-1767240 offers ways to increase the flexibility of a stent in its radially compact delivery disposition. It suggests resorting to portions not parallel to the stent length, such as struts that are curved, or bridges that are skewed to the long axis of the stent.

SUMMARY OF THE INVENTION

The present invention is defined in the claims below in which different aspects are presented in respective independent claims, and dependent claims are directed to optional or preferred features. In one embodiment, the invention takes the form of a laser-cut stent in which the slits cut by the laser in the tubular workpiece that is the precursor of the stent are staggered with respect to each other, in the length direction of the stent cylinder such that the slits cut by the laser are, in general, all the same length but the struts created by cutting the laser slits are not all the same length because the axial stagger between circumferentially adjacent slits is arranged to be something other than half the common slit length. However, as the accompanying drawings will reveal, even when many of the slits can be made free of axial displacement (staggering) relative to the circumferentially next adjacent slits, the effect of eliminating head to head cusps on adjacent stenting rings can still be accomplished. As long as some of the adjacent slits are staggered, by an amount other than a one half slit length, the necessary circumferential displacement of facing cusps away from each other can still be achieved, as the slitted tube undergoes radial expansion.

DETAILED DESCRIPTION

Figure 1:
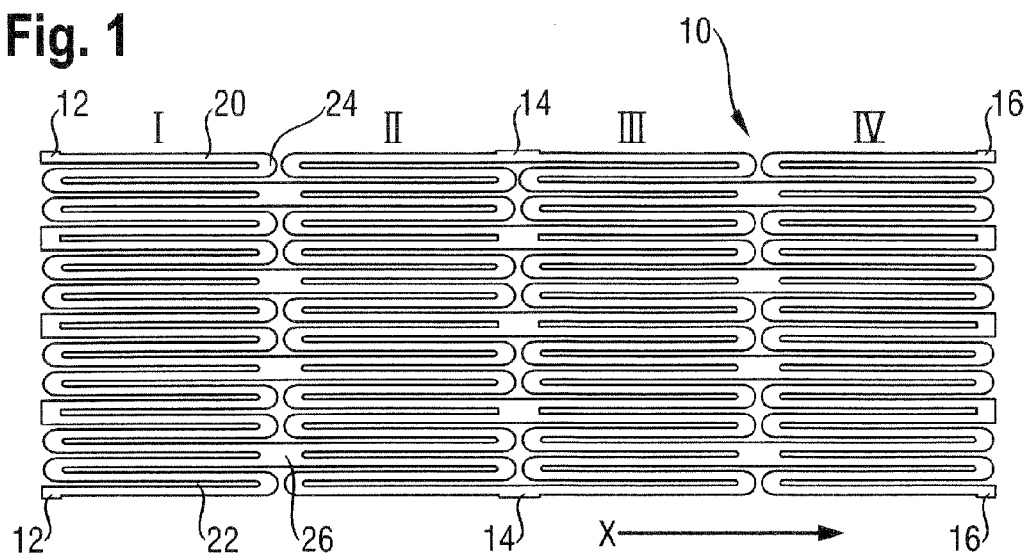
FIG. 1 is a view from above, of a slitted tube opened out flat

Referring to FIG. 1, we see a slitted tube 10, opened out flat by parting the slitted tube at interface portions 12, 14 and 16 to display, opened out flat, a succession of stenting rings I, II, III, IV arranged next to each other along the length of the slitted tube parallel to its long axis direction X. Each of the four stenting rings exhibits a serial progression of $n_r$ struts, here 24 struts, (20) separated from each other by the slits through the wall thickness of the tubular workpiece, the succeeding struts of each stenting ring being joined by successive cusps 24. In the unexpanded slitted configuration of FIG. 1, each cusp is in "head-to-head" relationship, along the axis direction X of the slitted tube, with a cusp of the adjacent stenting ring. As can be seen, each stenting ring is connected to the next adjacent stenting ring by four bridges 26 distributed at regular intervals (90°) around the circumference of the slitted tube. The number of bridges per ring is $n_s$ and the number of struts between successive bridges is $n_b$ so: $n_r = s \cdot n_b$.

In stent technology, particularly stents made of shape memory alloy (NITINOL), a strut matrix made by slitting a precursor tube is conventional.

Figure 2:
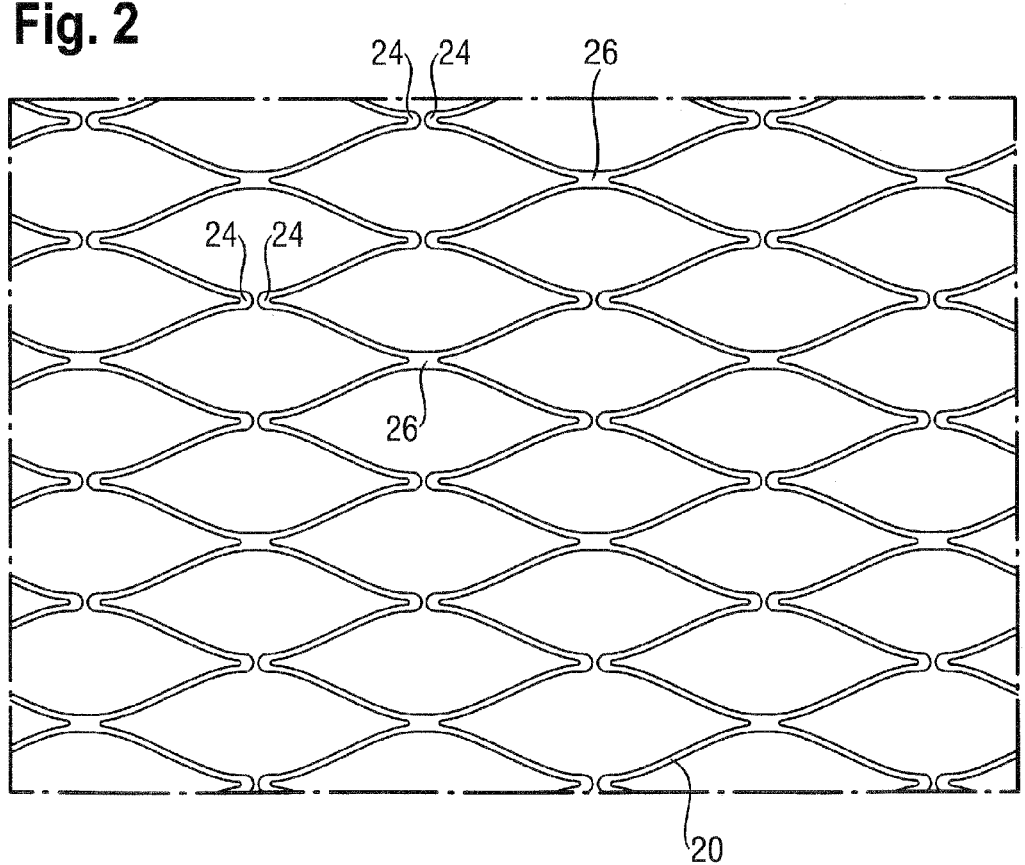
FIG. 2 shows a portion of the matrix of FIG. 1, radially expanded (but also opened out flat)

Turning to FIG. 2, we see a portion of the FIG. 1 slitted tube radially expanded so that the struts of each stenting ring are inclined to the axial direction X and present themselves as a zig-zag sequence of struts around the circumference of the stent. It will be noted that the cusps 24 of adjacent stenting rings are still in head-to-head disposition. Skilled readers will appreciate that any gross bending of a deployed stent is liable to bring opposing cusps on the inside of the bend into physical contact with each other.

Figure 3:
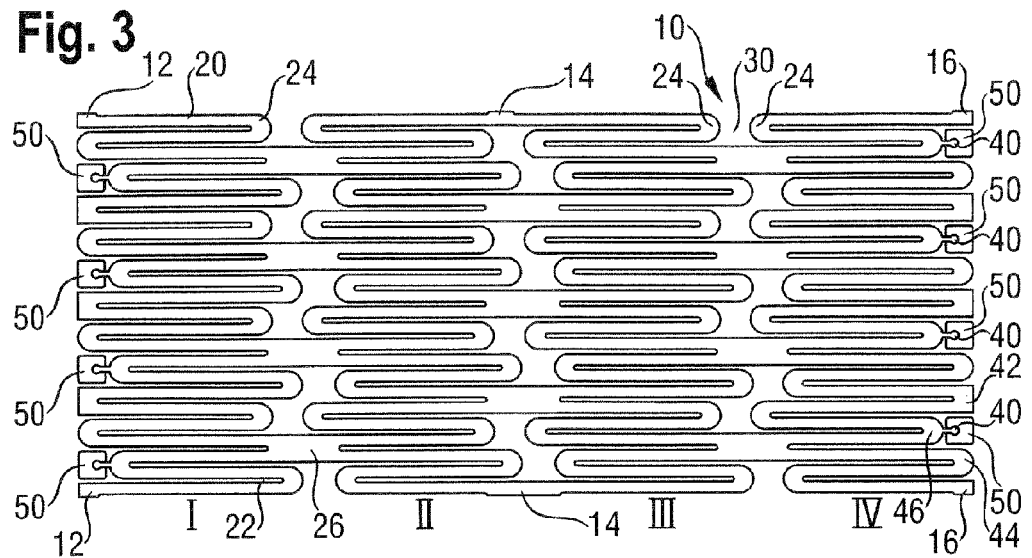
FIG. 3 shows another embodiment of slitted tube opened out flat.

Turning to FIG. 3, we can recognise the same pattern of 24 struts 20 making up 4 adjacent stenting rings I, II, III, IV, recognisably equivalent to what is shown in FIG. 1. Further, just as in FIG. 1, each cusp 24 is in head-to-head relationship with a cusp of the next adjacent stenting ring. Just as in FIG. 1, each stenting ring is connected to the next adjacent stenting ring by four bridges 26.

However, the slits 22 in the tube 10, that have created the strut matrix, are axially staggered relative to each other, in a way which is not present in drawing FIG. 1. In consequence of this axial staggering, there is also axial staggering of the gaps 30 between each pair of facing cusps 24. In FIG. 3, there is shown a greater axial separation between facing cusps 24 than is apparent from FIG. 1, but this is not the decisive difference between the FIG. 1 concept and that of FIG. 3.

Reverting to FIG. 1, and concentrating on a pair of struts defining between them an individual gap 22, one can see that the axial length of the two struts, one each side of the slit 22 1 is the same. However, when we look at FIG. 3, and a particular slit 22, we notice that the length of the strut that extends down each side of the slit 22, from the common cusp 24 at one end of the slit, are different. This has repercussions for the way the struts deform when the slitted tube of FIG. 3 is radially expanded, to the zig-zag pattern shown in FIG. 4.

Figure 4:
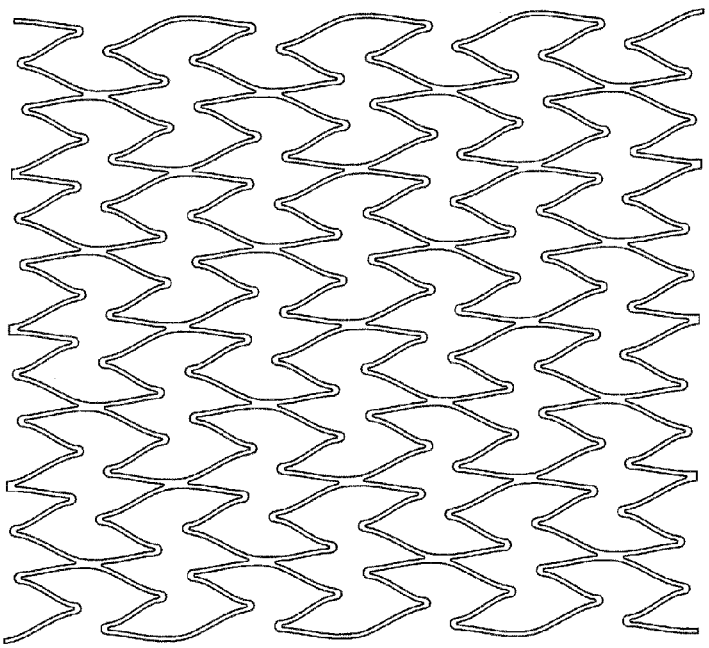
FIG. 4 shows the FIG. 3 strut matrix, opened out flat, and expanded.

Comparing FIG. 4 with FIG. 2, it is immediately evident that there are no longer pairs of cusps 24 facing each other, head to head. Instead, each cusp points towards a gap between two adjacent cusps of the adjacent zig-zag stenting ring. The skilled reader will appreciate that when the stent of FIG. 4 is bent (into a banana shape) each cusp is free to advance axially into the gap between two adjacent cusps of the adjacent stenting ring, rather than striking, head on, the facing cusp of the adjacent stenting ring, as in FIG. 2.

Figure 5:
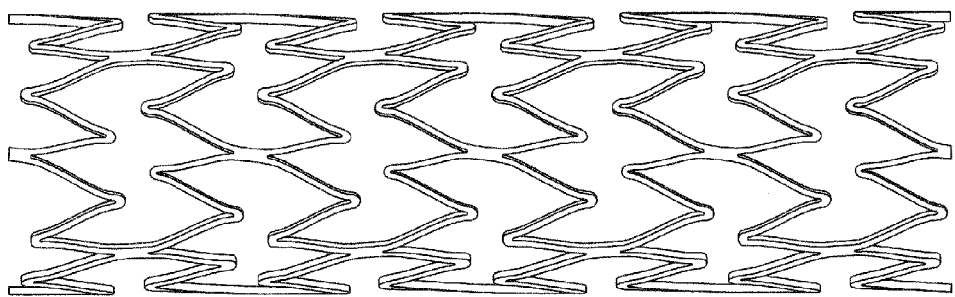
FIG. 5 is a perspective view of the FIG. 4 strut matrix, not opened out flat

FIG. 5 is a perspective view but shows the same phenomenon as is drawn in drawing FIG. 4 I with the same strut matrix.

Figure 9:
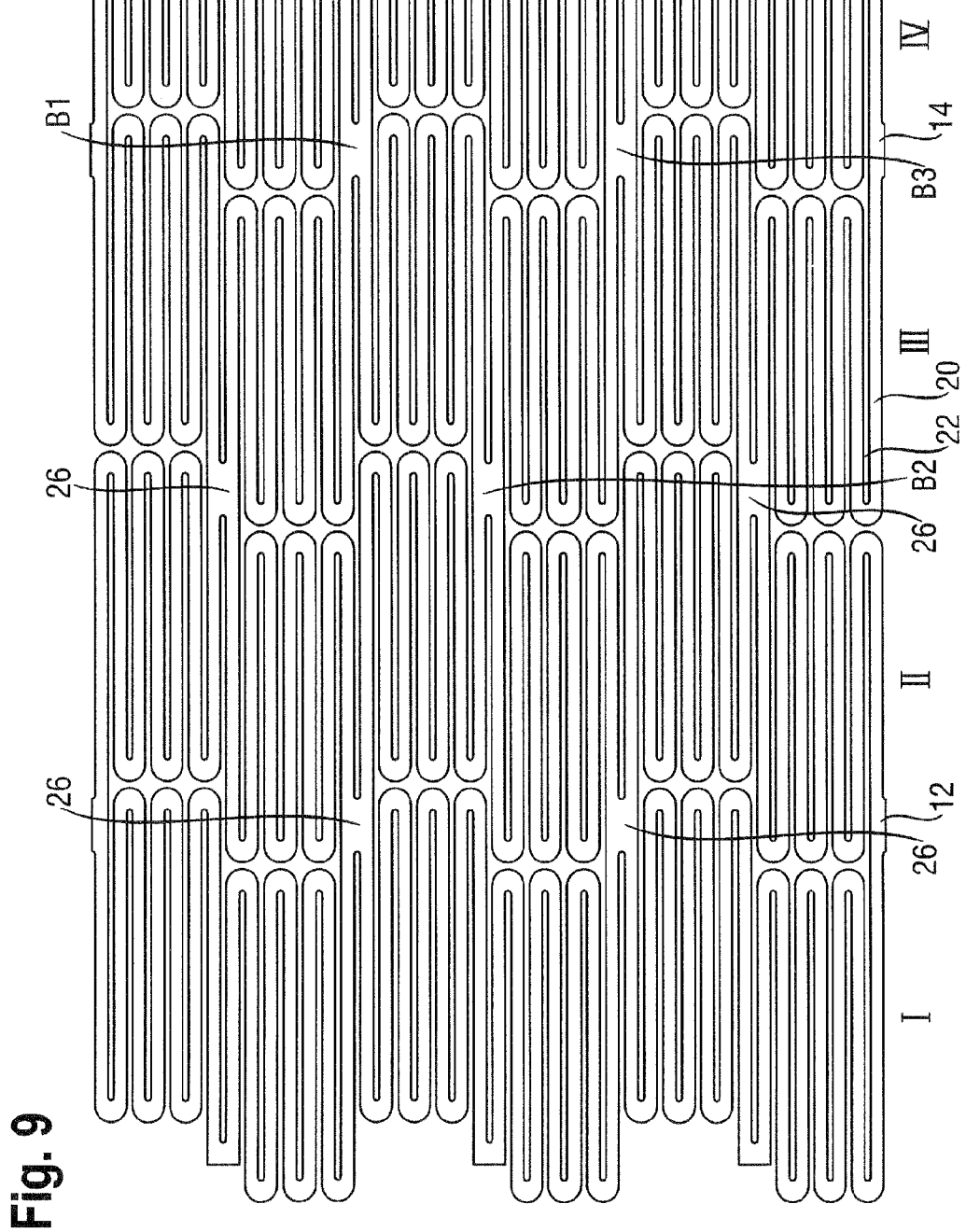
FIG. 9 is a view from above, like that of FIGS. 1, 3 and 6 but of yet another embodiment of a slitted tube opened out flat.

The skilled reader will grasp that the number of struts in each stenting ring need not be 24, and the number of bridges between adjacent stenting rings need not be four. Another arrangement that shows promise is one in which each stenting ring has 42 struts and adjacent stenting rings are connected by three bridges distributed at 120° intervals. Such an arrangement is shown in FIG. 9 1 and is described below.

Figure 6:
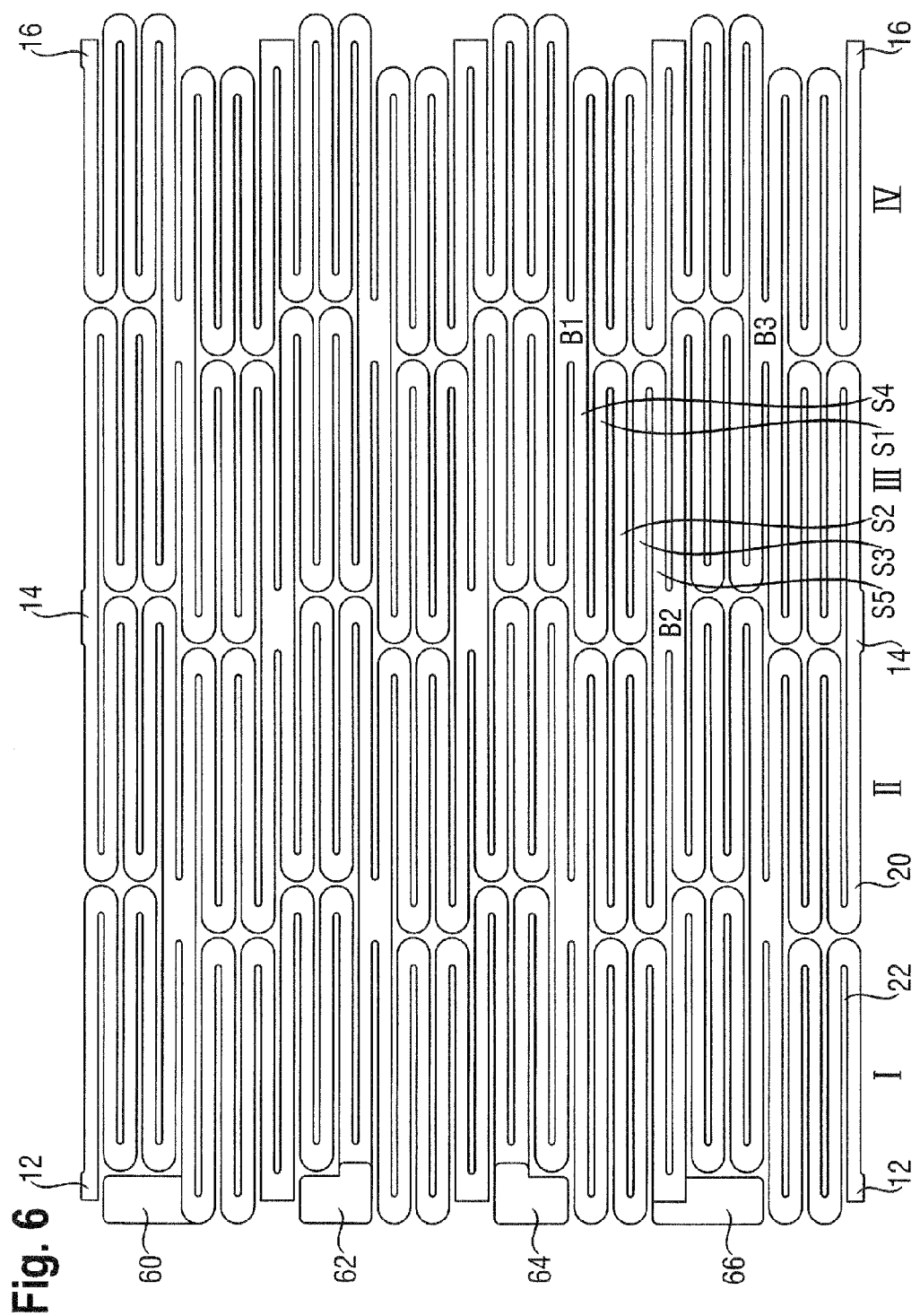
FIG. 6 is a view of another slitted tube opened out flat.
Figure 7:
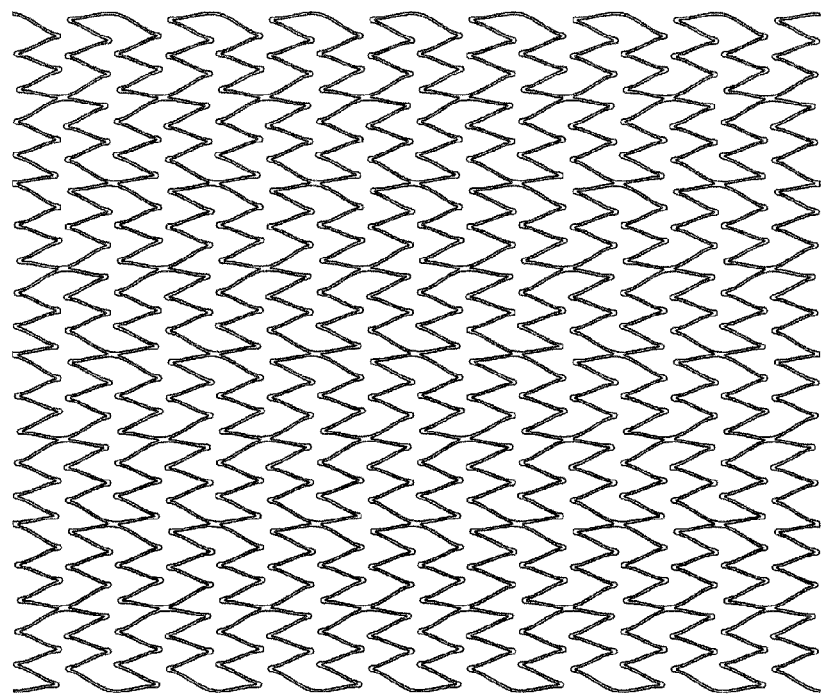
FIG. 7 is a view of the slitted tube of FIG. 6, radially expanded and opened out flat
Figure 8:
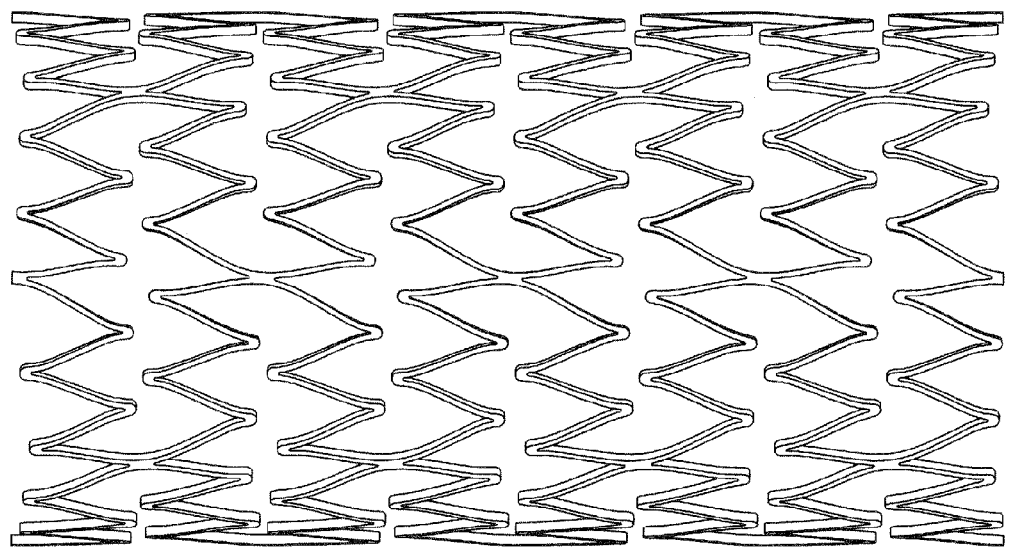
FIG. 8 is a perspective view of the radially expanded tube of FIGS. 6 and 7.

FIGS. 6, 7 and 8 show another attractive design, namely, a slitted tube with 40 struts per ring and four bridges. Since other aspects of the design are described above with reference to FIGS. 3 and 4, the same reference numbers are used to identify corresponding features. of the design. Again, it can be seen that when the FIG. 6 slitted tube is opened out radially, the cusps 24 automatically move to positions where they are no longer facing head to head any cusp of the adjacent zig-zag stenting ring, with consequential advantages of avoiding cusp to cusp contact when the deployed stent is subjected to bending deformation.

In FIG. 6, in loop III, three successive bridges are labeled B1, B2, B3. Bridges B1and B3 connect loop III to loop IV. Bridge B2 is one of the four bridges that connect loop III. Between bridges B1 and B2, and between bridge B2 and B3, is a sequence of five struts. Three of these struts S1, S2, S3, have the same length. Each extends between two free cusps. The other two struts, S4 and S5, have lengths different from each other. This length difference is what takes the free cusps of adjacent loops out of a head-to-head facing relationship in the expanded configuration of the stent, as can be understood from FIGS. 7 and 8, which also reveal that the bridges are correspondingly skewed, relative to the long axis of the stent, in the expanded disposition of the stent.

The lengthwise staggering of cusps that characterises the present invention can deliver useful technical effects that include the following.

When a self-expanding strut is to be released from its catheter delivery system, the usual way is to withdraw proximally, relative to the stent, a restraining sheath that surrounds its abluminal surface. When all cusps in a loop are at the same point along the axis of the stent, all can spring radially outwardly from the sheath simultaneously. This impulsive release is not ideal for controlled release. Axial staggering of cusps can assist in releasing the stent more progressively and steadily, cusps escaping one by one from the inward radial confinement of the proximally retreating sheath.

For some stents, the design features non-identical proximal and distal ends, so that it is critically important to load the stent in the delivery system with its distal end nearer the distal end of the delivery system. An advantage of the present invention is that it permits the building of stents with identical distal and proximal ends, that are indifferent to the choice of stent end to lie closer to the distal end of the delivery system.

The axial staggering opens up possibilities for "recesses" such as recesses 40 in FIG. 3, where radiopaque marker elements 50 can be located. These elements thus lie snug between circumferentially spaced apart cusps 42, 44 and axially adjacent to intervening cusps 46, to which it will be convenient to attach the marker. Any axial pushing on the stent, while the confining sleeve is withdrawn is customarily applied to the end surface of the stent. By locating markers in the end recesses and arranging for the end elevation of the stent to comprise both cusps and markers, the stresses on the end elevation are distributed around the circumference as evenly as possible, and over the maximum area of surface of the implant, which is good for fatigue performance, quality control, and efficiency of stent release. Finally, with markers recessed into the end zone of a stent, the markers when imaged give a true impression of where the stent matrix is, and where it is not. A short look at US 2006/0025847 serves to reveal the advantages of the present proposal over another recent proposal to deal with pushing forces.

Not to be underestimated is the advantage yielded by this invention, that a "peak-to-valley" distribution of cusps in the expanded deployed disposition is automatic, regardless how short are the bridges between adjacent stenting loops. Short, strong, robust bridges that connect axially adjacent stenting loops are greatly to be welcomed, for many reasons. In particular/they are less vulnerable to inadvertent straining (bad for fatigue performance if nothing else) when stent matrices are being installed in a catheter delivery system, or when being deployed out of one. Put another way, the stent with short stubby bridges can be rated for greater loads imposed on it during loading or deployment. Since the radial force that a stent can exert on surrounding bodily tissue increases with the number of stenting loops per unit (axial) length of the stent, a reduction in the length of the bridges connecting axially adjacent stenting loops will give rise to an increased stenting force.

However, short stubby bridges are disadvantageous, to the extent that they prejudice stent flexibility. The more flexible a stent is, the better its resistance to fatigue failure (other things being equal). One way to deliver more flexibility, despite an absence of much flexibility in the bridges, is to increase the number of struts in the sequence of struts between each bridge and the next bridge. On that basis, the arrangement of FIG. 9, with 7 struts between any two bridges B1, B2 or B2, B3, is superior to the FIG. 6 design with 5 struts, itself superior to that of FIG. 3, with 3 struts.

When it comes to radiopaque markers, it is important to arrange the markers so that they are distributed around the circumference of the stent, in the radially compact delivery disposition of the stent, as evenly as is practicable. In FIG. 3, the arrangement is even. FIG. 6 shows one possible arrangement of tantalum markers 60, 62, 64, 66 which is not far from an even distribution in the compact form of the stent (although further from evenly distributed when the stent is expanded). In the FIG. 9 design it is clear that each end of the stent offers only three recesses for installation of a set of three markers evenly distributed around the circumference of the stent.

The markers can be of different shapes, in order to meet these design objectives, as is illustrated in FIG. 6, as one example.

One thing that is striking about the present invention is how it delivers a simple pattern of linear slits in the compact configuration that exhibits in each stenting loop a sequence of stepwise displacements, up and down the axis of the stent, in the positions of the free cusps, yet, in the expanded disposition of the stent, the axial steps are gone. Instead, the bridges are skewed, and the free cusps are circumferentially displaced, relative to the free cusps of the adjacent stenting loop that were facing them, head-to-head, in the compact disposition. Of significance is that, in the expanded disposition, when the stent must exert radially outward stenting force on the bodily tissue that forms the wall of the stented bodily lumen, the zig-zag struts of each stenting rings march around the circumference of the lumen in a progression in which axial displacement of free cusps, relative to each other, is difficult to discern. Instead, the stenting loops deploys in a way that is close to an optimal planar hoop, transverse t the axis, for generating a large mechanical radially outward stenting force.

Applicant's WO 2007/135090 discloses a stent that is "bend-capable" in that cusps move out of a "head-to-head" facing relationship in the expanded deployed stent, when the stent tube is bent out of a straight configuration. It will be apparent to the skilled reader that the present invention (lengthwise staggering of cusps) can be combined with the invention of WO 2007/135090 (skewed unit cell) to deliver a stent matrix that avoids a head to head facing relationship of cusps, regardless of the extent to which the stent is bent out of a straight line after deployment. One way to accomplish the result explained in WO 2007/135090 is to arrange the strut matrix such that n 8/2 is an even number.

It hardly needs to be added, that the stents taught in this disclosure can be used in the same way as prior art stents are used. They can carry graft material, or drugs, for example. They can be delivered transluminally, by a suitable catheter delivery system. They can carry radiopaque markers, as is taught in the state of the art. They will find particular application in situations where the stent, after deployment, is subject to a high degree of bending.

The present drawings show specific embodiments which are to be assessed as exemplary, not limiting. The stent need not be made from shape memory metal and need not be laser cut. The inventive concept disclosed herein is applicable to a wide range of known stent technologies.

What is claimed is:

1. A stent comprising
   a matrix of struts disposed parallel to one another comprising:
      a plurality of loops disposed along a longitudinal axis of the stent comprising:

end-zone loops composed of tied cusps, free cusps and radiopaque markers;
and
intermediate-zone loops composed of tied cusps and free cusps,
wherein tied cusps and free cusps of end-zone loops and intermediate-zone loops connect adjacent struts;
and
a bridge connecting a tied cusp of one loop head-to-head with a tied cusp of an adjacent loop
wherein all of the free cusps on one end of the end-zone loop and all of the radiopaque markers of the end-zone loop are disposed to touch a notional circle transverse to the longitudinal axis of the stent such that the stress imposed on the stent by a pushing annulus is shared among all of the free cusps and all of the radiopaque markers on the one end of the end-zone loops;
wherein the radiopaque markers are distributed around the circumference of the end-zone loops, each of the markers positioned in a gap defined between outer surfaces of adjacent end cusps;
and
wherein the adjacent struts connected by a tied cusp have different lengths, and at least one free cusp in each loop joins two struts of approximately equal length.

2. The stent according to claim 1 wherein free cusps of adjacent loops are circumferentially displaced from one another.

3. The stent according to claim 2, wherein each intermediate loop includes either 24, 40, or 42 struts.

4. The stent according to claim 3 wherein the stent includes 40 struts in each loop and 4 bridges connecting each pair of adjacent loops, and at least three consecutive struts having approximately equal lengths located between adjacent bridges.

5. The stent according to claim 3 wherein the stent includes 42 struts in each loop and 3 bridges connecting any two loops, and at least five consecutive struts having approximately equal lengths located between adjacent bridges.

6. The stent according to claim 2 wherein the bridges between any two adjacent intermediate-zone loops are evenly distributed around the circumference.

7. The stent according to claim 6 wherein radiopaque markers in an end zone of the stent are evenly spaced around the circumference.

8. The stent according to claim 7 wherein at least two radiopaque markers have shapes different from each other.

9. The stent according to claim 8 wherein at least three radiopaque markers each have a different shape from one another.

10. The stent according to claim 1 wherein there are N struts between two successive bridges connecting two adjacent loops A and B, N being an integral even number, and N/2 being an integral odd number.

11. The stent according to claim 1 wherein there are N struts between successive bridges connecting two adjacent loops A and B, N being an integral even number, and N/2 being also an integral even number.

12. The stent according to claim 1 wherein at least three radiopaque markers have a different shape from one another.

* * * * *